United States Patent [19]

Ohm et al.

[11] Patent Number: 4,933,186
[45] Date of Patent: Jun. 12, 1990

[54] DIHYDROPYRIDINE DEPOT FORMULATION

[75] Inventors: Andreas Ohm, Neuss; Helmut Luchtenberg, Niederkassel; Manfred Bücheler, Overath; Josef Schmoll, Wermelskirchen; Roland Rupp, Leichlingen; Eduard Porges, Cologne, all of Fed. Rep. of Germany; Takaaki Nishioka, Koka, Japan

[73] Assignee: Bayer Aktiengesellschaft, Leverkusen, Fed. Rep. of Germany

[21] Appl. No.: 228,636

[22] Filed: Aug. 4, 1988

[30] Foreign Application Priority Data

Aug. 11, 1987 [DE] Fed. Rep. of Germany ....... 3726666
Mar. 26, 1988 [DE] Fed. Rep. of Germany ....... 3810350

[51] Int. Cl.$^5$ ............................................. A61K 9/42
[52] U.S. Cl. .................................. 424/476; 424/474; 424/480; 424/482; 427/3
[58] Field of Search ............... 424/474, 482, 480, 476, 424/470; 427/3

[56] References Cited

U.S. PATENT DOCUMENTS

| | | | |
|---|---|---|---|
| 3,708,489 | 1/1973 | Rucker et al. | 514/929 X |
| 3,996,234 | 12/1976 | Bossert et al. | 514/929 X |
| 4,001,390 | 1/1977 | Ohno et al. | 424/480 |
| 4,252,786 | 2/1981 | Weiss et al. | 424/480 X |
| 4,309,405 | 1/1982 | Guley et al. | 424/21 |
| 4,421,738 | 12/1983 | Yamagiwa et al. | 424/480 X |
| 4,529,733 | 7/1985 | Gittos et al. | 514/929 X |
| 4,654,206 | 3/1987 | Okuda et al. | 424/480 X |
| 4,803,081 | 2/1989 | Falk et al. | 424/480 X |

FOREIGN PATENT DOCUMENTS

| | | |
|---|---|---|
| 0137198 | 4/1985 | European Pat. Off. |
| 0164588 | 12/1985 | European Pat. Off. |
| 0205282 | 12/1986 | European Pat. Off. |
| 0222411 | 5/1987 | European Pat. Off. |

*Primary Examiner*—Thurman K. Page
*Attorney, Agent, or Firm*—Sprung, Horn, Kramer & Woods

[57] ABSTRACT

A pharmaceutical formulation tablet with a long-lasting action for 1 to 2 daily doses having a diameter between about 0.5 and 15 mm and comprising
(a) a rapid-release core of a dihydropyridine,
(b) a coat containing no active compound and formed of a free-flowing powder mixture or of granules, and
(c) optionally, a further coating of a rapid-release dihydropyridine formulation.

12 Claims, 1 Drawing Sheet

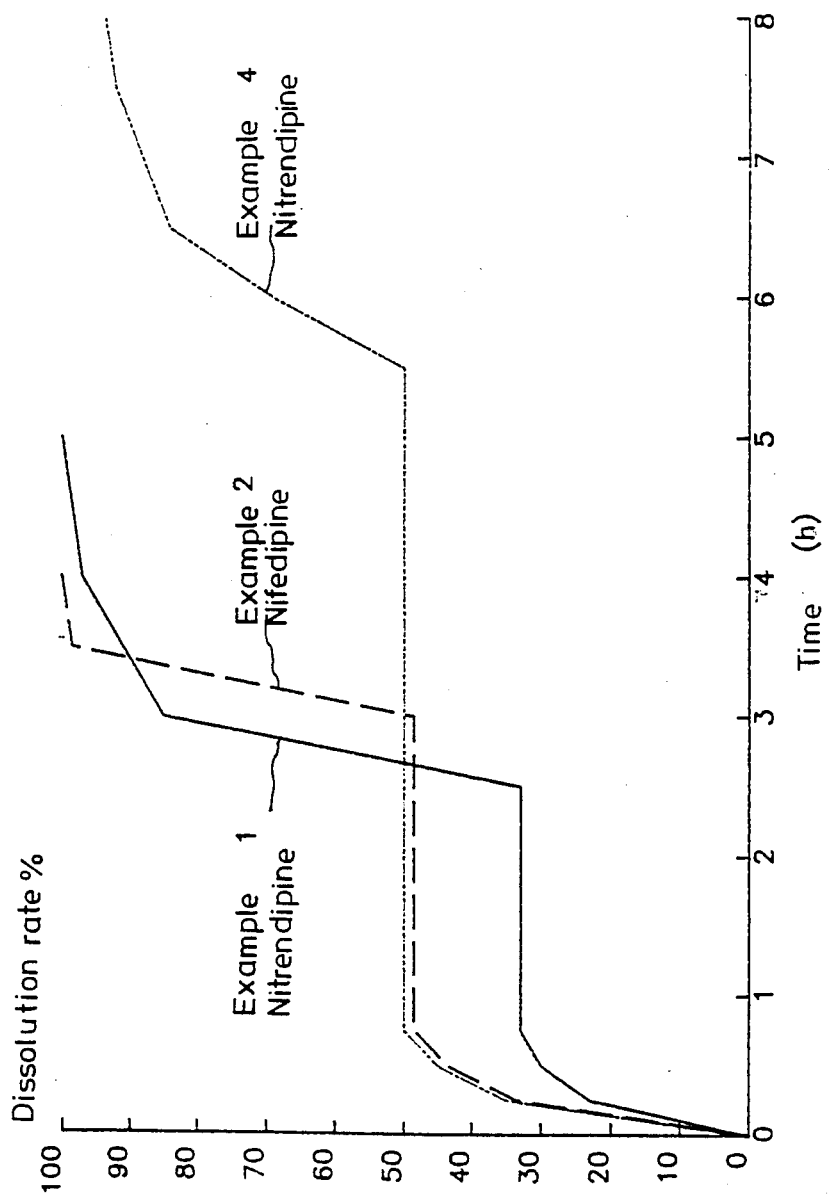

DIHYDROPYRIDINE DEPOT FORMULATION

The invention relates to solid pharmaceutical formulations with a long-lasting action for dihydropyridines, consisting of a rapid-release core with, located around it, a coat which delays the onset of release, and to processes for the preparation thereof.

Active compounds from the dihydropyridine class of substances and the use thereof as cardiovascular agents have already been disclosed (compare British Patent No. 1,173,862, British Patent No. 1,358,951, U.S. Pat. No. 4,256,749, German Offenlegungsschrift No. 3,311,003 and U.S. Pat. No. 4,264,611). Difficulties often occur in the pharmaceutical formulation of these potent active compounds, because the substances have only very low solubility, are often sensitive to light, and their absorbability in biological systems often gives to rise to problems.

Some dihydropyridines additionally have particular pharmacokinetics: their metabolism takes place predominantly during the first pass through the liver (so-called first pass effect), which takes place immediately after absorption of the active compound. Moreover, with these active compounds, the metabolism rate depends on the rate of arrival of the active compound in the liver: as the amount per unit time increases, the percentage of active compound degraded decreases (so-called saturable first-pass effect). The bioavailability of the active compound then depends on the in vivo rate of release of the active compound.

Numerous attempts have been made to prepare optimum pharmaceutical formulations which improve the bioavailability of these potent active compounds. Thus, for example, some active compounds have been dissolved in special organic solvent systems and introduced into gelatin capsules in order to ensure a rapid and effective onset of action (compare British Patent No. 1,362,627). Attempts have also been made to convert dihydropyridines such as nifedipine by use of water-soluble polymers into coprecipitates or "solid solutions" in order to improve the bioavailability (compare British Patent No. 1,579,818). Furthermore, for example, nifedipine formulations with a prolonged duration of action have been described, these containing crystalline nifedipine with a chosen specific surface area (compare EP-A No. 0,047,899). However, these pharmaceutical formulations have the disadvantage that the plasma levels fall after a few hours, and thus diminutions in the action may occur. In contrast, towards the end of the absorption time, the formulations according to the invention exhibit a burst of active compound which results in a higher activity rate and means that a reliable action is achieved even with single daily doses.

It is desirable for the treatment of diseases which have to be treated for prolonged periods, such as, for example, hypertension, to minimize the frequency of intake of medicaments. This is not only more pleasant for the patient, it also increases the reliability of treatment by diminishing the disadvantages of irregular intakes and results in a more nearly constant course of active compound concentrations in the body. At the same time, this minimizes the risk of undesired over- or under-dosages. Use of the formulations according to the invention results in avoidance of blood level peaks after intake of rapid-release forms, and diminution of the risk due to intake being irregular or forgotten when the dose frequency is high.

Particularly advantageous are dosage forms with which the delivery of active compound is appropriate for the patient's requirements Thus, for example, a diurnal rhythm has been described for the changes in blood pressure (compare Lemmer B.; Chronopharmakologie, Tagesrhythmen und Arzneimittelwirkung [Chronopharmacology, diurnal rhythms and drug action], Wiss. Verlag GmbH Stuttgart (1984)) according to which both the normotensive and the hypertensive values (systolic) fall to a minimum during the night (about 4 a.m.) and then rise again steeply in the early hours of the morning, that is to say even while sleep continues. The blood pressure then reaches a maximum at about 10 a.m. A blood pressure medicament adjusting to the diurnal rhythm would have the advantage over previous depot systems that the patient would be exposed to active compound only when the latter is required by the body. In particular, the steep rise in the blood pressure which takes place in the early hours of the morning even while sleep continues can be reliably dealt with by delivery of relatively large amounts of active compound from the core, without the body being exposed to unnecessary active compound in the preceding hours of the night with their normal fall in blood pressure. Thus, with an evening intake of the formulation according to the invention it is possible to ensure an optimum blood plasma concentration appropriate for the biological diurnal rhythm of the patient.

There is a need to make available both to the physician and to the patient, for example for the long-term therapy of cardiovascular disorders, the highly active dihydropyridines in a form such that, if possible, one daily dose suffices for treatment of the disease.

Pharmaceutical formulations with delayed release of active compound (depot forms) have already been described for dihydropyridines. Thus, for example, attempts have been made to prepare a slow release formulation by a specific particle size distribution of the crystalline active compound or by a selected specific surface area of the active compound crystals (compare German Offenlegungsschrift No. 3,033,919). Furthermore, special tablet formulations which, on the principle of the osmotic pump, release the active compound over a prolonged period from the interior of a tablet, which is surrounded by a semipermeable lacquer layer, through an opening which has previously been provided, and thus achieve a depot effect (compare U.S. Pat. No. 3,916,899).

The hitherto known forms with delayed delivery of active compound, especially those for dihydropyridines, have a number of disadvantages. Either their depot action is restricted to only a few hours so that, as a rule, there is a continuing need for the patient to take two or more doses a day, or the rate of release of the active compound decreases markedly after a few hours, so that the blood levels may also fall below the limit required for efficacy.

With the abovementioned osmotic system, depending on the contents of the capsule used, local irritation of the tissue in the stomach or intestinal tract may occur due to excessive concentrations. Furthermore, a flattening of the release curve in the terminal region is also observed with this osmotic delayed action principle. Owing to the nature of the osmotic system, part of the active compound may remain in the drug form and thus not be available for the desired absorption. Moreover, the preparation of this drug form is very elaborate because organic solvents have to be used in the process for the preparation therof, and the lacquer layer of each tablet must be drilled individually using special techniques, for example using a laser beam.

Moreover, in the case of the abovementioned dihydropyridines, which have a bioavailability which depends on the in vivo release rate, the continuously releasing depot formulations hitherto mentioned result in comparatively low bioavailability.

It is likewise known from the state of the art to coat pharmaceutical formulations with an enteric lacquer. With the pharmaceuticals, a part or all of the dose of the active compound is not released from the drug form until it has left the stomach. These discontinuously releasing depot forms are unreliable merely by reason of their pH-dependence of liberation of active compound, because the residence times in the stomach vary widely from patient to patient and, moreover, depend greatly on food intakes (residence times in the stomach about 0.2–12 h). Although it is possible with a drug form of this type to release a part of the active compound after a time lag, for the abovementioned reasons this delay period (lag time) is not reproducible so that, for example, it is not possible with these to achieve reliable adjustment to biological processes which depend on diurnal rhythms.

It has now been found that solid pharmaceutical formulations with a long-lasting action for 1 to a maximum of 2 daily doses, consisting of a rapid-release core and of a coating which delays the onset of release are particularly suitable for dihydropyridine active compounds and, surprisingly, ensure high efficacy and a reliable time course of absorption.

The invention relates to solid pharmaceutical formulations with a long-lasting action for 1 to a maximum of 2 daily doses, consisting of a rapid-release core and of a coating which delays the onset of release, containing at least one dihydropyridine of the general formula I

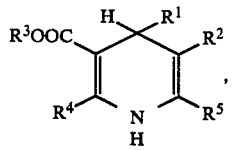

in which $R^1$ represents a phenyl radical which carries one or two identical or different substituents from the group comprising nitro, halogen or trifluoromethyl, or represents the radical

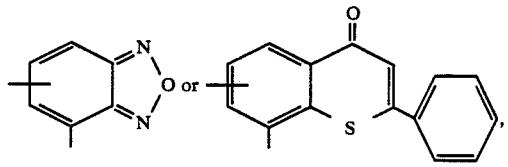

$R^2$ represents a nitro group or represents the radical $COOR_6$, with $R^6$ denoting alkyl which has 1 to 10 C atoms and which is optionally substituted by alkoxy having 1 to 4 C atoms or by one or more halogens, or $R^2$ together with $R^5$ represents the lactone group $-CO-O-CH_2-$, $R^3$ represents alkyl which has 1 to 10 C atoms and which is optionally substituted by alkoxy having 1 to 4 C atoms or by one or more fluorines, and $R^4$ and $R^5$ are identical or different and each represents alkyl which has 1 to 4 C atoms and which is optionally substituted by hydroxyl, with the core/coat dosage form (a) consisting of a core which contains at least one of the abovementioned dihydropyridines in a rapid-release form, and (b) consisting of a coat which is located around the core, contains no active compound and only slowly dissolves in an aqueous medium, and (c) where appropriate additionally containing on the coat a rapid-release initial dose of the dihydropyridine active compound, with the diameter of the form being between 0.5 and 15 mm.

Preferred formulations are those which contain in the core 20–100 percent by weight, preferably 40–100 percent by weight, in particular 50–100 percent by weight, of the total dihydropyridine active compound in the dosage form.

If a rapid-release initial dose is applied to the coat, this preferably contains 10–80 percent by weight, in particular 15–50 percent by weight, of the total amount of dihydropyridine.

Depending on the nature of the active compound, the formulations according to the invention contain a total of, preferably, 1 to 200 mg, in particular 10 to 150 mg, of at least one active compound from the dihydropyridine class.

The rapid-release core of the formulation contains the active compound preferably in amorphous form or in finely ground or micronized crystalline form.

A core with rapid release is to be understood preferably to be those cores which contain the dihydropyridine active compound in non-depot form and release it to the extent of at least 75% in a time not exceeding 1 hour under the following release conditions: USP paddle method using "sink conditions", that is to say conditions such that the type and amount of the aqueous release medium are chosen such that it is able to dissolve at least three times the amount of active compound used.

The term "sink conditions" may be explained further as follows: 4 l of 0.1N hydrochloric acid +0.1 to 0.5% wetting agent such as Tween 80 or Texapon K12 (sodium lauryl sulphate); 37° C.; 100 rpm.

The known dihydropyridines nifedipine, nitrendipine, nisoldipine and nimodipine are of particular interest.

If the rapid-release core contains amorphous dihydropyridine, the latter is preferably dissolved together with water-soluble polymers such as polyvinylpyrrolidone, methylcellulose, hydroxypropylcellulose or hydroxypropylmethylcellulose in an organic solvent such as acetone, methylene chloride, chloroform or lower aliphatic alcohols. In this connection, it is expedient to use 2 to 10 parts by weight, in particular 3 to 8 parts by weight, of the water-soluble polymers to 1 part by weight of dihydropyridine, and to prepare corresponding coprecipitates from them.

If the rapid-release core contains dihydropyridines in crystalline form, it is preferable to use dihydropyridine crystals with a maximum mean particle size of 25 μm, in particular a maximum mean particle size of 15 μm. The particle size is determined by the cilas method (literature: A. Buerkholz et al., Part. Charact 1, 1984, 153–160, "Laser diffraction spectrometers/experience in particle size analysis").

When a crystalline dihydropyridine is used in the core, it is expedient to add auxiliaries which are readily soluble in water, such as, for example, lactose. It is likewise possible, by the use of disintegrants such as, for example, crosslinked polyvinylpyrrolidone (PVP), or by surface-active substances such as, for example, sodium lauryl sulphate, to increase the rate of release.

The coat contains no active compound. The coat material is formed by a hydrophilic gel-forming polymer mixed with pharmaceutically customary auxiliaries such as, for example, lactose, starch, cellulose, citric acid and the like, and magnesium stearate as lubricant. This hydrophilic polymer controls the rate of dissolution and the erosion of the coating The factors controlling the rate of dissolving away/erosion of the coat material are, inter alia, the thickness of the layer of coating and the ratio of polymer(s) to the remaining auxiliaries.

Examples of suitable hydrophilic gel-forming polymers are modified starches and cellulose-like polymers such as, for example, methylcellulose, hydroxypropylmethylcellulose, hydroxypropylcellulose and sodium carboxymethylcellulose, and, where appropriate, suitable modulators are hydrophobic auxiliaries such as hydrogenated castor oil, calcium stearate and magnesium stearate, stearic acid, cetyl palmitate and waxes such as, for example, beeswax.

The rates of erosion and dissolution of the coat can also be controlled via the different degrees of viscosity of the polymer, with the rate being increased when low-viscosity types are used and becoming slower when high-viscosity types are used. The concentration of the polymer in the coat material is normally 5–100%, preferably 10–90%. The concentration which is used depends on the degree of viscosity of the polymer(s) and on the solubility/hydrophilicity of the auxiliaries, and the amount thereof, which are used.

Examples of suitable solid dosage forms for the core/coat principle according to the invention are pellets and press-coated tablets. The size of the formulation can vary from 0.5 to 15 mm, with the lower range being suitable and preferred for pellets and the range above 5 mm being suitable and preferred for tablets.

A particular advantage when pellets are used lies in the division of the total dose of active compound into several subunits (so-called multiple dose), which permits pellets with coats of various thicknesses or of various compositions to be combined in such a way that the desired release profile of the dosage forms containing the total dose (for example hard gelatin capsule) can be adjusted, for example a linear delivery of active compound, a continuous increase in the rate of release of the active compound, or a pulsatile delivery of the active compound in bursts at different times. In this case, the initial dose can be introduced by, for example, uncoated active compound cores Moreover, it is possible by combining pellet populations with different lag periods to minimize the dose in such a way that the blood plasma concentrations do not leave the therapeutic range, and the risk of side effects is diminished.

In the case of press-coated tablets it is possible to apply an initial dose to the placebo coat so that a discontinuous release in bursts is achieved by this.

The desired lag times for the release of active compound from the core can be controlled via the thickness of the coat layer and the proportions of the delaying agents. The set lag time until the active compound in the core is released due to erosion away of the coat material determines the desired depot effect. In this connection, the lag time due to erosion/dissolving away of the coat is virtually unaffected by the pH.

It ought to be expressly pointed out that the depot formulation according to the invention differs from the hitherto known core/coat formulations in that the coat contains no active compound, and the core contains the active compound in rapid-release form.

The press-coated tablet according to the invention is prepared by customary methods which are explained by the following process as an example: the rapid-release core containing active compound is initially prepared by means of customary tableting processes, for example from powder mixtures or from granules, and then a placebo coat which contains no active compound is placed around this core with the aid of a tablet-coating press (for example a Kilian Presscoater), with the coat material consisting of a free-flowing powder mixture or of granules which have been obtained by dry or wet granulation, and with, where appropriate, a lacquer layer, which where appropriate also contains an initial dose of the active compound, being applied, with the aid of customary lacquer-coating methods, for example by spraying on or by pressing on another layer, to the press-coated tablets obtained in this way.

The coated pellets according to the invention are likewise prepared by customary methods, for example in granulators or in pelleting units which allow build-up granulation, for example, in a pelleting dish, a rotary granulator, a fluidized bed granulator or a coating drum, with the pellet cores being either prepared separately beforehand or built up directly and continuously, and then the coating material being applied.

The use of rotary granulators is particularly advantageous.

Customary known pharmaceutical measures such as, for example, the lacquer-coating of the core, the use of flavorings and aromatizing substances and lubricants and customary auxiliaries, which are familiar to the pharmaceutical expert, can, of course, also be used for the formulation according to the invention.

Multilayer tablets based on casein matrices and containing two or three layers, each of which in turn can contain active compounds, have already been described in the state of the art (compare U.S. Pat. No. 3,184,386). In contrast to the present invention, the tablets described therein contain active compound in the outer coating.

U.S. Pat. No. 3,558,768 also describes press-coated tablets which contain active compounds in slow-release form both in the core and in the coat. According to this U.S. Patent Specification, the rates of release can vary, but the forms are in every case slow-release.

Press-coated tablets which contain no active compound in the coat material are also described in Il Farmaco, No. 3, March 84, 67 et seq (Conte et al.). However, the kinetics of release from these tablets differs markedly from the core/coat principle according to the invention described here after a lag time the active compound is released continuously with zero order kinetics over a long time. In this case, the coat material serves as a diffusion barrier and not for setting up release of the active compound which takes place discontinuously in bursts. In contrast to the present core/coat principle according to the invention, the "reservoir press-coated tablet" can be used only for active compounds having a certain minimum solubility in water.

Salomon et al. (Pharm. Ind. 41. No. 8, pages 799 et seq. 1979) also describe press-coated tablets which contain no active compound in the coating material. Once again, the release takes place continuously (with root time kinetics). The statements made above apply in principle. Another dosage form which has a beneficial effect specifically on the saturable first-pass effect of psoralens is described in DE No. 3,115,033 A 1. However, in this case, the coat material contains active compound Moreover, the delay until active compound is released from the core of the press-coated tablets or pellets is achieved not by applying large proportions of hydrophilic gel-forming polymers (coat) but by lacquer-coating the core/pellets (a thin lacquer film).

German Offenlegungsschrift No. 2,651,176 describes pellets with controlled delivery of active compound The formulations mentioned therein differ from the coated formulations according to the invention from the outset since they also contain active compound in the coating. In addition, the formulations described therein can be obtained only in elaborate processes by applying many layers, whereas the press-coated tablet according to the invention is prepared simply by compression and, in the case of the coated pellets, only one layer is applied by a continuously operating process to the rapid-release cores.

The principle of the formulation according to the invention results in avoidance of the customary disadvantages of known depot forms as well as of hitherto known multilayer or press-coated tablets and pellets and of forms based on the osmotic principle. In particular, for example, it is possible to avoid the rate of release of the active compound being low, because of the desired depot nature of the formulation, and thus the need to accept, for example, lower bioavailabilities of active compounds because of a saturable first-pass effect. On the contrary, when press-coated tablets or coated pellets with a uniform lag time are used, the entire active compound is released relatively rapidly, but in discontinuous bursts, in order to achieve the desired depot effect.

This intermittent release, which takes place at time intervals which can be predetermined and is, moreover, not pH-dependent, means that the formulation according to the invention differs from all hitherto known delaying principles for solid dosage forms. It is believed that this formulation will result in increased bioavailability, especially in the case of active compounds which have saturable first-pass kinetics.

Another advantage of the drug forms according to the invention is that they are particularly suitable for those active compounds which show greater absorption in lower sections of the gastrointestinal tract, for example in the large intestine, than in the stomach or in the small intestine. It is possible, by appropriate design of the coat, to determine the lag period in such a way that the active compound is released in the effectively absorbing part of the gastrointestinal tract, by which means it is possible to achieve high bioavailability and a reliable effect.

In addition, the technology according to the invention also permits adjustment of the release of active compound to the diurnal rhythm of the blood pressure.

Another advantage which may be mentioned is the simplicity of the preparation technology.

In the case of the coated pellets (drug form for example capsule) a further additional advantage which should be mentioned is the possibility of setting any desired kinetics of release of the active compound (by combining different coated pellets). It is possible in this way almost to "tailor" a depot formulation of this type to meet the requirements of a given active compound.

In view of the need, which has existed for a long time, for pharmaceutical forms with a long-lasting action, it is more than surprising that no-one has hitherto described or prepared the coated drug form with a rapid-release core according to the invention, which is simple to prepare and very effective. The present invention means that the patient can be put in the position of needing only one daily dose of the medicament, which represents a more reliable and more pleasant mode of treatment, especially for long-term therapy.

The curves in FIG. 1 show, for some selected examples according to the invention, the principle of discontinuous release of active compound, especially the aimed-at release bursts, which can be set to take place some hours after the dose, virtually independently of the pH.

EXAMPLES

EXAMPLE 1

| Core | nitrendipine microfine | 8.0 mg |
|---|---|---|
| | lactose | 8.0 mg |
| | cellulose microcrystalline | 8.0 mg |
| | cross-linked PVP | 16.0 mg |
| | are mixed and granulated with: | |
| | PVP 25 | 4.0 mg |
| | sodium lauryl sulphate | 0.8 mg |
| | water | q.s. |
| | after drying, the following is added | |
| | magnesium stearate | 0.2 mg |
| | and tablets are formed by compression: | |
| | weight | 45.0 mg |
| | format diameter | 5.0 mm |
| Coat | hydroxypropylcellulose type L | 50.0 mg |
| | hydroxypropylcellulose type M | 87.5 mg |
| | lactose | 111.0 mg |
| | are mixed and granulated with water, where appropriate, use a part of the hydroxypropylcellulose for the granulation). After drying, the following is added: | |
| | magnesium stearate | 1.5 mg |
| | the core and coat granules are compressed in a tablet-coating press to give press-coated tablets: | |
| | weight | 295.0 mg |
| | format diameter | 9.0 mm |
| Initial dose | 4 mg of nitrendipine are lacquered onto the press-coated tablet by customary processes. The lacquer consists of nitrendipine, hydroxypropylmethylcellulose and polyethylene glycol. It rapidly releases the active compound. | |

The in vitro release of the active compound from this lacquered press-coated tablet is shown in FIG. 1.

EXAMPLE 2

| Core: | nifedipine microfine | 5.0 mg |
|---|---|---|
| | lactose | 38.8 mg |
| | corn starch | 15.0 mg |
| | are mixed and granulated with starch paste: | |
| | corn starch | 1.0 mg |
| | water | q.s. |
| | after drying, the following is added: | |
| | magnesium stearate | 0.2 mg |
| | cellulose microcrystalline | 5.0 mg |

-continued

| | | |
|---|---|---|
| | and tablets are formed by compression: | |
| | weight | 65.0 mg |
| | format diameter | 6.0 mm |
| Coat: | hydroxypropylcellulose type M | 126.0 mg |
| | lactose | 145.6 mg |
| | are mixed and granulated with water, where appropriate, use a part of the hydroxypropylcellulose for the granulation). After drying, the following is added: | |
| | magnesium stearate | 8.4 mg |
| | Core and coat granules are compressed in a tablet-coating press to give press-coated tablets: | |
| | weight | 345.0 mg |
| | format diameter | 9.0 mm |
| Initial dose: | A second layer of granules containing active compound (composition as described under "core") is pressed onto the press-coated tablet, 5 mg dose of nifedipine. | |

The in vitro release of the active compound from this bilayer press-coated tablet is shown in FIG. 1.

EXAMPLE 3

| | | |
|---|---|---|
| Core: | nisoldipine microfine | 10.0 mg |
| | lactose | 12.0 mg |
| | cellulose microcrystalline | 10.0 mg |
| | PVP cross-linked | 7.5 mg |
| | are mixed and granulated with: | |
| | PVP 25 | 2.5 mg |
| | sodium lauryl sulphate | 0.5 mg |
| | water | q.s. |
| | after drying, the following is added: | |
| | magnesium stearate | 0.2 mg |
| | PVP cross-linked | 2.3 mg |
| | and tablets are formed by compression: | |
| | weight | 45.0 mg |
| | format diameter | 5 mm |
| Coat: | hydroxypropylcellulose type L | 31.0 mg |
| | hydroxypropylcellulose type M | 106.0 mg |
| | lactose | 111.5 mg |
| | are mixed and granulated with water, where appropriate, a part of the hydroxypropylcellulose is used for the granulation). After drying, the following is added: | |
| | magnesium stearate | 1.5 mg |
| | Core and coat granules are compressed in a tablet-coating press to give press-coated tablets: | |
| | weight | 295 mg |
| | format diameter | 9 mm |
| Initial dose: | 10 mg of nisoldipine are lacquered onto the press-coated tablets using the customary methods and lacquering auxiliaries (compare, for example, Example 1). | |

EXAMPLE 4

| | | |
|---|---|---|
| Core: | as Example 3, but containing nitrendipine microfine in place of nisoldipine microfine. | |
| Coat | as Example 3 | |
| Press-coated tablet: | weight: | 295.0 mg |
| | format diameter | 9.0 mm |
| Initial dose: | as Example 3, but nitrendipine microfine in place of nisoldipine microfine. | |

The in vitro release of the active compound from these lacquered press-coated tablets is shown in FIG. 1.

EXAMPLE 5

| | | |
|---|---|---|
| Core: | as Example 2, but additionally containing 2.5 mg of ethyl 2-methyl-4-(4-oxo-2-phenyl-4H-thiochromen-8-yl)-5-oxo-1,4,5,7-tetra-hydrofuro[3,4-b]-pyridine-3-carboxylate (core weight of 65 mg compensated with maize starch) | |
| Coat: | as Example 2 | |
| Initial dose: | a second layer of granules containing active compound (composition as described under "core") is pressed onto the press-coated tablets. | |

EXAMPLE 6

| | | |
|---|---|---|
| Core: | as in Example 4 | |
| Coat: | methylcellulose | 250.0 mg |
| | lactose | 65 mg |
| | are mixed and granulated with water where appropriate, a part of the methylcellulose is used for the granulation). After the drying, the following is added: | |
| | magnesium stearate | 5.0 mg |
| | Core and coat granules are compressed in a tablet-coating press to give press-coated tablets: | |
| | weight | 365.0 mg |
| | format diameter | 9.0 mm |
| Initial dose: | as in Example 4 | |

EXAMPLE 7

| | | |
|---|---|---|
| Core: | as in Example 5 | |
| Coat | pregelatinized starch | 225 mg |
| | lactose | 90 mg |
| | are mixed and granulated with water. After the drying, the following is added: | |
| | magnesium stearate | 5 mg |
| | and press-coated tablets are formed by compression: | |
| | weight | 385.0 mg |
| | format diameter | 9.0 mm |

EXAMPLE 8

A rotary granulator is used to prepare pellets which are built up as follows:

| | | |
|---|---|---|
| Core: | diameter: 1.00–1.25 mm | |
| | composition: | |
| | nitrendipine microfine | 70% |
| | hydroxypropylcellulose type L | 28% |
| | sodium lauryl sulphate | 2% |
| Coat: | composition: | |
| | pregelatinized starch | 30% |
| | hydroxypropylcellulose type M | 40% |
| | hydrogenated castor oil | 30% |
| | amount applied (based on the core weight): depends on the desired lag time, can be set as desired, for example | 300% |

EXAMPLE 9

A coating drum is used to prepare pellets which are built up as follows:

| | |
|---|---|
| Core: | diameter: 0.63–0.8 mm |

|         | -continued                             |      |
|---------|----------------------------------------|------|
|         | composition:                           |      |
|         | nisoldipine microfine                  | 70%  |
|         | hydroxypropylcellulose type L          | 28%  |
|         | sodium lauryl sulphate                 | 2%   |
| Coat:   | composition:                           |      |
|         | hydrogenated castor oil                | 70%  |
|         | hydroxypropylcellulose type M          | 30%  |
|         | amount applied (based on the core weight): |  |
|         | 1. 0%                                  |      |
|         | 2. 100%                                |      |
|         | 3. 200%                                |      |
|         | 4. 300%                                |      |
|         | Pellets 1–4 are mixed in such a way that 30 mg of nisoldipine microfine are distributed on the pellets as follows: | |
|         | 13% of the dose - pellet 1             |      |
|         | 16% of the dose - pellet 2             |      |
|         | 27% of the dose - pellet 3             |      |
|         | 44% of the dose - pellet 4             |      |
|         | The pellet mixture is dispensed into hard gelatin capsules. | |

EXAMPLE 10

| Core: | nimodipine microfine | 70% |
|-------|----------------------|-----|
|       | hydroxypropylcellulose type L | 28% |
|       | sodium lauryl sulphate | 2% |
|       | are mixed and converted by pelleting with water as granulating liquid into spherical particles with a mean diameter of 0.5–1.5 mm. | |
| Coat: | Nimodipine cores and coating powder are mixed together in a continuously operating, rotary granulator and water is added as granulating liquid. The coating/powder mixture has the following composition: | |
| 10(a) | cellulose microcrystalline | 86% |
|       | calcium stearate | 9% |
|       | hydroxypropylcellulose type M | 5% |
| 10(b) | rice starch | 20% |
|       | castor oil hydrogenated | 50% |
|       | hydroxypropylcellulose type M | 30% |
| 10(c) | cellulose microcrystalline | 70% |
|       | stearic acid | 15% |
|       | sodium carboxymethylcellulose / hydroxypropylmethylcellulose mixture (1:1) | 10% |
| 10(d) | pregelatinized starch | 30% |
|       | hydroxypropylcellulose type M | 40% |
|       | hydrogenated castor oil | 30% |
| 10(e) | hydrogenated castor oil | 70% |
|       | hydroxypropylcellulose type M | 30%. |

The coating powder mixtures of Examples 10a–e are applied to the cores in the following amounts:
Example 10 a—150% of the core weight
Example 10 b—250% of the core weight
Example 10 c—100% of the core weight
Example 10 d—300% of the core weight
Example 10 e—150% of the core weight.

It will be appreciated that the instant specification and claims are set forth by way of illustration and not limitation, and that various modifications and changes may be made without departing from the spirit and scope of the present invention.

What is claimed is:

1. A pharmaceutical formulation tablet with a long-lasting action for 1 to 2 daily doses having a diameter between about 0.5 and 15 mm and comprising
   (a) a rapid release core comprising an initial dose formulation of at least one dihydropyridine of the formula

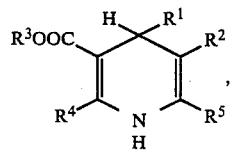

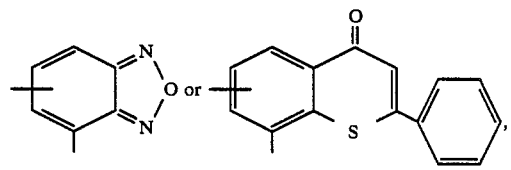

in which
R$^1$ represents a phenyl radical which carries one or two identical or different substituents from the group consisting of nitro, halogen or trifluoromethyl, or represents the radical R$^2$ represents a nitro group or represents the radical COOR$_6$, with R$_6$ denoting alkyl which has 1 to 10 C atoms and which is optionally substituted by alkoxy having 1 to 4 C atoms or by one or more halogens, or
R$^2$ together with R$^5$ represents the lactone group —CO—O—CH$_2$—,
R$^3$ represents alkyl which has 1 to 10 C atoms and which is optionally substituted by alkoxy having 1 to 4 C atoms or by one or more fluorines, and
R$^4$ and R$^5$ each independently represents alkyl which has 1 to 4 C atoms and which is optionally substituted by hydroxyl, and
   (b) A coat which is located around the core, contains no pharmaceutically active dihydropyridine compound and only slowly dissolves in an aqueous medium, and
   (c) a further coating containing a rapid-release dihydropyridine formulation.

2. A process for the preparation of a tablet according to claim 1, comprising
   (a) pressing a mixture of powders or granules of the rapid release dihydropyridine to form cores,
   (b) coating the cores with a coat containing no active compound and formed of a free-flowing powder mixture or of granules, and
   (c) coating the active-compound-free coat with a second coating containing a rapid-release dihydropyridine formulation.

3. A tablet according to claim 1, containing in the core about 20 to 100 percent by weight of the total content of active dihydropyridine compound.

4. A tablet according to claim 1, containing a total of about 1 to 200 mg of dihydropyridine active compound.

5. A tablet according to claim 1, wherein the rapid-release core contains the dihydropyridine active compound in amorphous form or in finely ground or micronized crystalline form.

6. A tablet according to claim 1, wherein the rapid-release core contains amorphous dihydropyridine together with about 2 to 10 times its weight of at least one water-soluble polymer selected from the group consisting of polyvinylpyrrolidone, methylcellulose, hydroxypropylcellulose and hydroxypropylmethylcellulose.

7. A tablet according to claim 1, wherein the core contains the dihydropyridine active compound in crystalline form with a maximum mean particle size of about 25 μm.

8. A tablet according to claim 1, wherein the coat, which contains no active compound, contains a hydrophilic gel-forming polymer.

9. A tablet according to claim 8, wherein hydrophilic gel-forming polymer is selected from the group consisting of methylcellulose, hydroxypropylmethylcellulose and hydroxypropylcellulose.

10. A tablet according to claim 8, wherein the coat further contains a hydrophobic auxiliary selected from the group consisting of hydrogenated castor oil, calcium stearate, magnesium stearate, stearic acid, cetyl palmitate and a wax.

11. A process for the preparation of pellets according to claim 1, comprising
 (a) forming a mixture of powders or granules of the rapid release dihydropyridine into cores in a pelleting unit or granulator, and
 (b) coating such cores with the active-compound-free composition in a pelleting unit or granulator.

12. A process for the preparation of pellets according to claim 11, wherein the coating is effected in a rotary granulator.

* * * * *